(12) United States Patent
Pendo et al.

(10) Patent No.: US 7,514,038 B2
(45) Date of Patent: Apr. 7, 2009

(54) SENSOR SUBSTRATE AND METHOD OF FABRICATING SAME

(75) Inventors: Shaun Pendo, Santa Maria, CA (US); Rajiv Shah, Rancho Palos Verdes, CA (US); Edward Chernoff, Frazier Park, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 782 days.

(21) Appl. No.: 10/861,976

(22) Filed: Jun. 4, 2004

(65) Prior Publication Data

US 2004/0223875 A1 Nov. 11, 2004

Related U.S. Application Data

(62) Division of application No. 10/038,276, filed on Jan. 2, 2002.

(60) Provisional application No. 60/318,055, filed on Sep. 7, 2001.

(51) Int. Cl.
*G01N 21/00* (2006.01)
*H05K 3/40* (2006.01)
*H05K 1/03* (2006.01)

(52) U.S. Cl. ............... 422/58; 422/82.05; 438/762; 438/584

(58) Field of Classification Search ............ 204/430, 204/195; 438/622, 648, 762, 584; 128/899; 422/56, 94, 82.05; 257/698; 174/262
See application file for complete search history.

(56) References Cited

U.S. PATENT DOCUMENTS

| | | | |
|---|---|---|---|
| 4,240,438 A | 12/1980 | Updike et al. | |
| 4,343,688 A * | 8/1982 | Harwood | ............ 204/430 |
| 4,479,796 A | 10/1984 | Kallok | |
| 4,484,987 A | 11/1984 | Gough | |
| 4,568,335 A | 2/1986 | Updike et al. | |
| 4,628,928 A | 12/1986 | Lowell | |
| 4,650,547 A | 3/1987 | Gough | |
| 4,703,756 A | 11/1987 | Gough et al. | |
| 4,757,022 A | 7/1988 | Shults et al. | |
| 4,771,772 A | 9/1988 | DeWitt | |
| 4,890,620 A | 1/1990 | Gough | |

(Continued)

FOREIGN PATENT DOCUMENTS

EP 0 906 006 A2 3/1999

(Continued)

OTHER PUBLICATIONS

Supplemental European Search Report as issued by the EPO on Sep. 6, 2006.

(Continued)

*Primary Examiner*—Walter D Griffin
*Assistant Examiner*—Christine T Mui
(74) *Attorney, Agent, or Firm*—Foley & Lardner LLP

(57) ABSTRACT

A substrate with hermetically sealed vias extending from one side of the substrate to another and a method for fabricating same. The vias may be filled with a conductive material such as, for example, a fritless ink. The conductive path formed by the conductive material aids in sealing one side of the substrate from another. One side of the substrate may include a sensing element and another side of the substrate may include sensing electronics.

15 Claims, 17 Drawing Sheets

U.S. PATENT DOCUMENTS

| | | | | |
|---|---|---|---|---|
| 4,897,338 A | * | 1/1990 | Spicciati et al. | 430/314 |
| 4,911,168 A | | 3/1990 | Davis | |
| 4,994,167 A | | 2/1991 | Shults et al. | |
| 5,094,951 A | | 3/1992 | Rosenberg | |
| 5,231,054 A | * | 7/1993 | Kosugi | 438/648 |
| 5,266,688 A | | 11/1993 | Rosenberg | |
| 5,328,460 A | | 7/1994 | Lord et al. | |
| 5,446,246 A | | 8/1995 | Desai | |
| 5,497,772 A | | 3/1996 | Schulman et al. | |
| 5,534,025 A | | 7/1996 | Moussy | |
| 5,569,186 A | | 10/1996 | Lord et al. | |
| 5,569,958 A | | 10/1996 | Bloom | |
| 5,593,852 A | | 1/1997 | Heller et al. | |
| 5,660,163 A | | 8/1997 | Schulman et al. | |
| 5,667,983 A | | 9/1997 | Abel et al. | |
| 5,683,758 A | | 11/1997 | Evans et al. | |
| 5,696,314 A | | 12/1997 | McCaffrey et al. | |
| 5,701,895 A | | 12/1997 | Prutchi et al. | |
| 5,707,502 A | | 1/1998 | McCaffrey et al. | |
| 5,711,868 A | | 1/1998 | Maley et al. | |
| 5,728,281 A | | 3/1998 | Holmstrom et al. | |
| 5,741,211 A | | 4/1998 | Renirie et al. | |
| 5,741,319 A | | 4/1998 | Woloszko et al. | |
| 5,770,028 A | | 6/1998 | Maley et al. | |
| 5,773,270 A | | 6/1998 | D'Orazio et al. | |
| 5,791,344 A | | 8/1998 | Schulman et al. | |
| 5,795,545 A | * | 8/1998 | Koripella et al. | 422/94 |
| 5,804,048 A | | 9/1998 | Wong et al. | |
| 5,919,216 A | | 7/1999 | Houben et al. | |
| 5,932,175 A | | 8/1999 | Knute et al. | |
| 5,941,906 A | | 8/1999 | Barreras, Sr. et al. | |
| 5,953,626 A | * | 9/1999 | Hause et al. | 438/622 |
| 5,965,380 A | | 10/1999 | Heller et al. | |
| 5,985,129 A | | 11/1999 | Gough et al. | |
| 5,992,211 A | | 11/1999 | Skrtic | |
| 6,001,067 A | | 12/1999 | Shults et al. | |
| 6,002,954 A | | 12/1999 | Van Antwerp et al. | |
| 6,027,479 A | | 2/2000 | Alei et al. | |
| 6,049,727 A | | 4/2000 | Crothall | |
| D424,696 S | | 5/2000 | Ray et al. | |
| D426,638 S | | 6/2000 | Ray et al. | |
| 6,093,167 A | | 7/2000 | Houben et al. | |
| 6,103,033 A | | 8/2000 | Say et al. | |
| 6,120,676 A | | 9/2000 | Heller et al. | |
| 6,122,536 A | | 9/2000 | Sun et al. | |
| 6,125,290 A | | 9/2000 | Miesel | |
| 6,125,291 A | | 9/2000 | Miesel et al. | |
| 6,134,459 A | | 10/2000 | Roberts et al. | |
| 6,135,978 A | | 10/2000 | Houben et al. | |
| 6,144,866 A | | 11/2000 | Miesel et al. | |
| 6,159,240 A | | 12/2000 | Sparer et al. | |
| 6,162,611 A | | 12/2000 | Heller et al. | |
| 6,163,723 A | | 12/2000 | Roberts et al. | |
| 6,165,892 A | * | 12/2000 | Chazan et al. | 438/623 |
| 6,175,752 B1 | | 1/2001 | Say et al. | |
| 6,198,952 B1 | | 3/2001 | Miesel | |
| 6,201,980 B1 | | 3/2001 | Darrow et al. | |
| 6,210,326 B1 | | 4/2001 | Ehwald | |
| 6,248,080 B1 | | 6/2001 | Miesel et al. | |
| 6,251,260 B1 | | 6/2001 | Heller et al. | |
| 6,261,280 B1 | | 7/2001 | Houben et al. | |
| 6,268,161 B1 | | 7/2001 | Han et al. | |
| 6,516,808 B2 | * | 2/2003 | Schulman | 128/899 |

FOREIGN PATENT DOCUMENTS

| | | | |
|---|---|---|---|
| JP | 04280657 | | 10/1992 |
| JP | 07022723 | | 1/1995 |
| JP | 2001-074681 | * | 3/2001 |
| WO | 198 32 052 A1 | | 2/1999 |
| WO | WO 99/48419 | | 9/1999 |
| WO | WO 01/01851 A1 | | 11/2001 |

OTHER PUBLICATIONS

Subminiature Implantable Potentiostat and Modified Commercial Telemetry Device for Remote Glucose Monitoring—IEEE Transactions on Instrumentation and Measurement, vol. 48, No. 6 Dec. 1999—Richard D. Beach Senior Member IEEE, Falko V. Kuster, and Francis Moussy, Member IEEE.

Supplemental European Search Report dated Dec. 12, 2008 for related European Patent Application No. 02780519.1-1265/1438029.

* cited by examiner

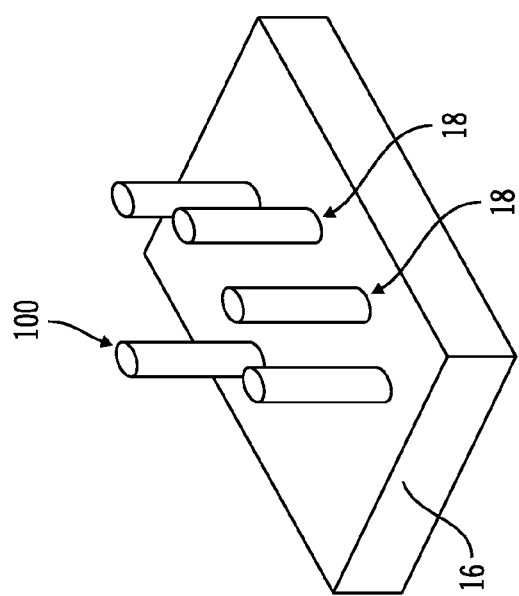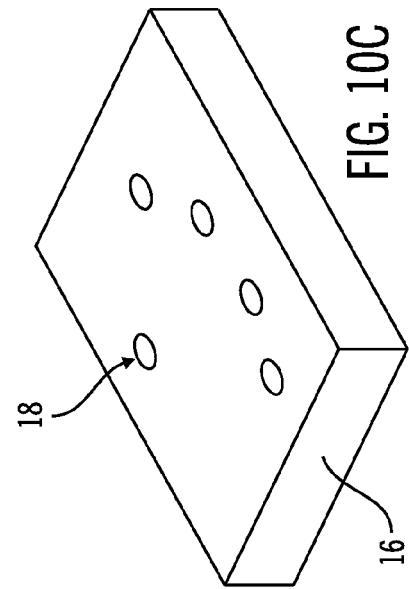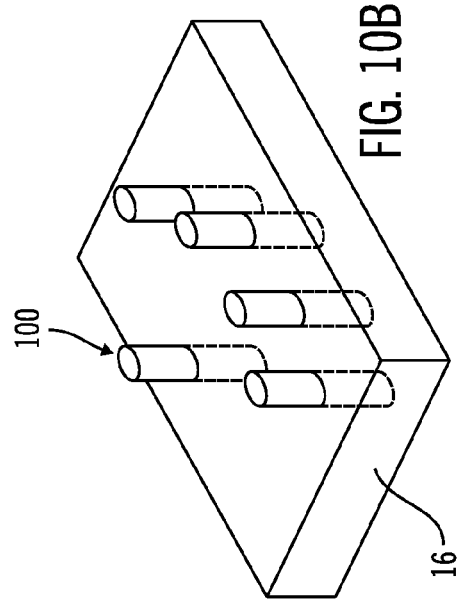

SENSOR SUBSTRATE AND METHOD OF FABRICATING SAME

CROSS-REFERENCE TO RELATED APPLICATIONS

This application is a divisional of application Ser. No. 10/038,276 filed Jan. 2, 2002, which is in turn claims the benefit of prior filed U.S. Provisional Patent Application No. 60/318,055; filed Sep. 7, 2001. The entirety of each which are incorporated herein by reference.

BACKGROUND

1. Field of the Invention

The present invention relates to the field of sensor technology and, in particular, to the formation of hermetically sealed substrates used for sensing a variety of parameters, including physiological parameters.

2. Description of Related Art

The combination of biosensors and microelectronics has resulted in the availability of portable diagnostic medical equipment that has improved the quality of life for countless people. Many people suffering from disease or disability who, in the past, were forced to make routine visits to a hospital or doctor's office for diagnostic testing currently perform diagnostic testing on themselves in the comfort of their own homes using equipment with accuracy to rival laboratory equipment.

Nonetheless, challenges in the biosensing field have remained. For example, although many diabetics currently utilize diagnostic medical equipment in the comfort of their own homes, the vast majority of such devices still require diabetics to draw their own blood and inject their own insulin. Drawing blood typically requires pricking a finger. For someone who is diagnosed with diabetes at an early age, the number of self-induced finger pricks over the course of a lifetime could easily reach into the tens of thousands. In addition, the number of insulin injections may also reach into tens of thousands. Under any circumstances, drawing blood and injecting insulin thousands of times is invasive and inconvenient at best and most likely painful and emotionally debilitating.

Some medical conditions have been amenable to automated, implantable sensing. For example, thousands of people with heart conditions have had pacemakers or defibrillators implanted into their bodies that utilize sensors for monitoring the oxygen content of their blood. Ideally, these sensors should be able to determine whether, for example, a person's heart is running very efficiently at a high heart rate or whether a person's heart has entered defibrillation. In order to effectively make this determination, an accurate sensor must be employed. Unfortunately, oxygen sensors implanted into the body have, thus far, typically required frequent and periodic checking and recalibration. In fact, one of the "holy grails" of the pacemaker industry has been an accurate, no drift, no calibration oxygen sensor. Up until now, such a sensor has been unavailable.

An ideal solution to the diagnostic requirements of those with disease or disability, absent an outright cure, is a sensor system that may be implanted into the body and that may remain in the body for extended periods of time without the need to reset or recalibrate the sensor. Regardless of the particular application for such a sensor system, in order to effect such a system the associated sensor must remain accurate, exhibit low drift and require no recalibration for extended periods of time. Such a system would typically require a sensor to be located in close proximity to sensing electronics in order to maintain the required characteristics.

However, attempts to place sensor electronics in close proximity to the sensor in implantable sensor systems have historically suffered from the environment in which they operate. For example, in an implantable sensor system for diabetics, a sensor is needed to detect an amount of glucose in the blood. Consequently, the sensor must be implanted within the body in such a manner that it comes into direct contact with the blood. However, in order to place the sensor electronics in such a system in close proximity to the sensor, the sensor electronics themselves must be placed into the blood as well. This poses obvious dangers for the sensor electronics. The sensor electronics must remain in electrical contact with the sensor; however, any exposure of the sensor electronics to the blood or any other fluid would potentially short circuit the sensor electronics and destroy the entire system.

Thus, an ideal implantable sensor system would provide for a sensor to be in close proximity to sensor electronics while also providing hermeticity between the sensor, which may be exposed to fluids, and the sensor electronics, which must remain free from short circuiting fluids. In addition, the required hermeticity must be maintained over the life of the sensing system. The present invention provides such a system.

SUMMARY OF THE DISCLOSURE

Embodiments of the present invention relate to sensor substrates and methods and systems for fabricating sensor substrates. According to embodiments of the present invention, a sensing apparatus may include a substrate having a first side for a sensing element and a second side for electronics. The sensing apparatus may also include a via or vias that make electrical contact from the first side of the substrate to the second side of the substrate. Additionally, the vias may be hermetically sealed from the first side of the substrate to the second side of the substrate.

According to another embodiment of the present invention, a sensing apparatus may include a substrate having a first area for a sensing element and a second area for electronics. The sensing apparatus may also include one or more vias making electrical contact from the first area of the substrate to the second area of the substrate. The via may be hermetically sealed from the first area of the substrate to the second area of the substrate and may be filled with a conductive material.

The via of the sensing apparatus may also be filled with a conductive material. The conductive material may be a fritted or fritless ink such as gold or platinum paste. The via may be covered by a cap made from alumina and deposited using an ion beam assist deposition process.

The substrate may be a ceramic such as substantially 92%-96% alumina. If desired, the substrate may be annealed.

A side of the substrate may be covered with a lid. The lid may be made of a metal such as gold.

According to an embodiment of the present invention, a method of forming an hermetically sealed substrate may include obtaining a substrate material; forming a via or vias from a first side of the substrate to a second side of the substrate; and filling the vias with a conductive material such that an hermetic seal forms between the first side of the substrate and the second side of the substrate.

The vias may be formed by laser drilling through the substrate. The substrate may be annealed after laser drilling.

The vias may be filled by placing a screen or a stencil on a surface of the substrate; pushing the conductive material through the screen such that the conductive material proceeds into the via; and pulling a vacuum on a side of the substrate opposite the side on which the conductive material has been pushed into the via such that the conductive material coats a wall of the via. Also, a meniscus may be formed that may also be filled. The meniscus may be filled by putting the substrate into a vacuum; printing a conductive material into the meniscus; and venting the substrate to atmosphere. After filling the meniscus the substrate may be annealed.

In addition, pillars may be deposited on top of the vias. Depositing pillars on top of the vias may include affixing a mask to the substrate; depositing a metal on top of the mask; removing the mask after depositing the metal; and coating the substrate with a ceramic. The metal may be dissolved after the substrate has been coated with the ceramic. The ceramic coating may be shorter than the pillar.

The via may be covered with a cap. The via may be covered with the cap using an ion beam assist deposition process.

These and other objects, features, and advantages of embodiments of the invention will be apparent to those skilled in the art from the following detailed description of embodiments of the invention when read with the drawings and appended claims.

BRIEF DESCRIPTION OF THE DRAWINGS

FIG. 10A is a perspective view of a substrate with aluminum pillars formed on top of vias according to an embodiment of the present invention.

FIG. 10B is a perspective view of a substrate with aluminum pillars formed on top of vias coated with an alumina coating according to an embodiment of the present invention.

FIG. 10C is a perspective view of the substrate after the aluminum pillars are dissolved.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Figure 1:
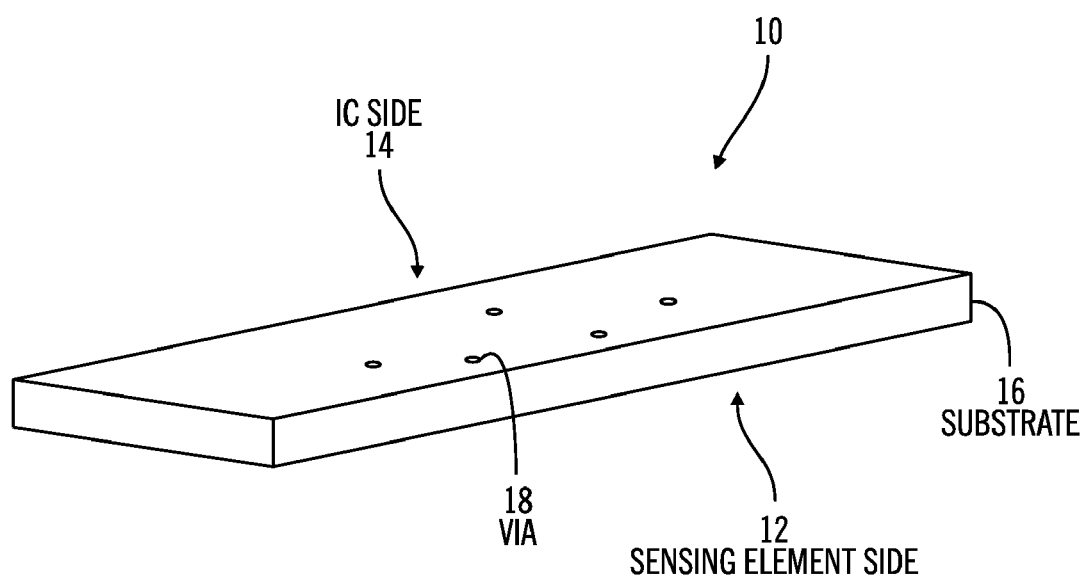
FIG. 1 is a perspective view of a generalized substrate configuration according to an embodiment of the present invention.

FIG. 1 shows a generalized substrate configuration according to an embodiment of the present invention. A sensor 10 has a sensing element side 12 of a substrate 16 on which a biosensing element, physiological parameter sensing element or other sensing element may be affixed. The sensor 10 also has an electronics side 14 of the substrate 16 on which electronics may be affixed for processing signals generated by the sensing element.

The sensing element side 12 may support any of a variety of sensing elements. For example, the sensing element may be a glucose sensor utilizing a glucose oxidase enzyme as a catalyst. Alternatively, the sensing element may be an oxygen sensor or may include a plurality of sensing element.

The electronics side 14 may support a variety of electronic circuits. According to one embodiment of the invention, the electronics side 14 of the substrate 16 may support an application specific integrated circuit (ASIC) containing data acquisition circuitry. Thus, analog signals received from the sensing element on the sensing element side 12 of the substrate 16 may be digitized by the ASIC on the electronics side 14 of the substrate 16. By positioning digitizing and other electronics close to the source of the analog signals and avoiding long cables along which signals are typically sent to be digitized, noise levels, offsets and signal loss are reduced. As a result, accuracy and reliability of the device is increased. In addition, once the signals have been digitized by the electronics on the electronics side 14 of the substrate 16, they may be sent to other devices for operation or other processing in discrete form rather than analog form, resulting in improved leakage, drift and other characteristics.

Figure 2A:
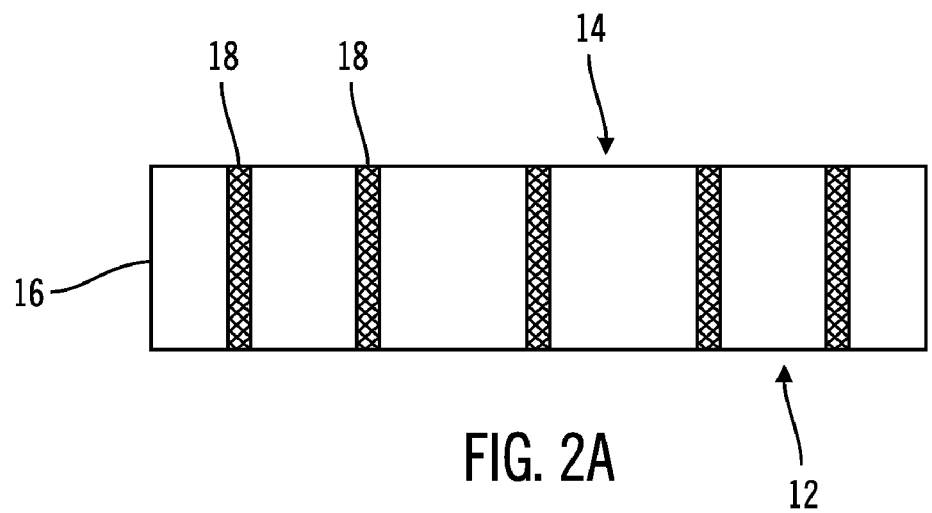
FIG. 2A is a cut-away view of vias extending through a substrate according to an embodiment of the present invention.

Extending from the sensing element side 12 of the substrate 16 to the electronics side 14 of the substrate 16 are vias 18. As shown in FIG. 2A, the vias 18 are pathways through the body of the substrate 16 that allow for electrical contact between an array of electrodes or other electrical contacts reacting with the sensing element on the sensing element side 12 of the substrate 16 and electronics on the electronics side 14 of the substrate 16.

Figure 2B:
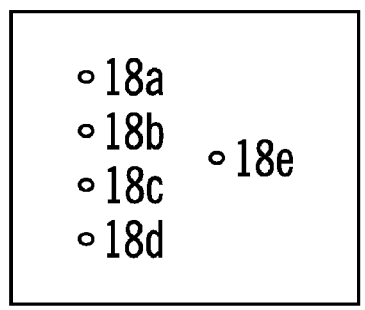
FIG. 2B is a top view of a via arrangement on a substrate according to an embodiment of the present invention.

The vias 18 may be arranged in a variety of fashions. A via arrangement for one sensing element according to one embodiment of the present invention may be seen in FIG. 2B. The via arrangement shown in FIG. 2B may correspond to electrodes that interact with an enzyme used as a catalyst in the sensing element. A first via 18a and a second via 18b correspond to a first working electrode and a first counter electrode. A third via 18c and a fourth via 18d correspond to a second working electrode and a second counter electrode. A fifth via 18e corresponds to a reference electrode. Electrodes will line up with the vias 18 using a process to be described below.

The generalized substrate configuration of electronics adjacent to a sensing element on opposite sides of the substrate 16 and the resulting ability to output discrete signals rather than analog signals from the sensor results in a stable device. Sensor electrode output drift of less than 5% over periods of one year or more may be possible using embodiments of the present invention. With such a low drift specification, replacement or calibration intervals may be greatly reduced, allowing embodiments of the present invention to be implanted into a human body for extended periods of time.

The generalized substrate configuration shown in FIG. 1 benefits from processes according to embodiments of the present invention, to be described below, that result in hermeticity between the sensing element side 12 of the substrate 16 and the electronics side 14 of the substrate 16. According to embodiments of the present invention, hermeticities corresponding to a helium leak rate of $1 \times 10^{-8}$ cc/sec at 1 atmosphere over a three year period may be obtained.

In addition, according to embodiments of the present invention, the sensor 10 may be implanted into the human body, residing in a vein or artery. In addition, the sensing element side 12 of the substrate 16 may be exposed to fluids, such as, for example, blood. In this type of use, should the fluids infiltrate the electronics on the electronics side 14 of the substrate 16, the fluids would destroy the electronics and render the device useless. However, because the electronics side 14 of the substrate 16 may be hermetically sealed from the sensing element side 12 of the substrate using processes according to embodiments of the present invention to be described below, electronics may be place directly on the electronics side 14 of the substrate 16 without exposure to fluids or other elements encountered by the sensing element that may damage the electronics.

The substrate 16 may be fabricated from a variety of materials. According to one embodiment of the present invention, the substrate 16 may be fabricated from ceramic. For example, the substrate 16 may be fabricated using a pressed ceramic slurry in tape form, which is widely available commercially. Also according to one embodiment of the invention, a substrate of 92%-96% alumina ($Al_2O_3$) is used. The substrate material may be bought in sheet form, which may be flexible or rigid.

The substrate 16 may take a variety of forms and may be structured in a variety of ways in addition to the configuration shown in FIG. 1. For example, according to one embodiment of the invention the substrate 16 may have more than two sides on which one or more sensing elements or electronics may be placed. The substrate 16 may be a multisurface device with sensing elements and electronics on any of multiple surfaces and having multiple vias extending in a variety of geometries to effect electrical contact between surfaces.

In another embodiment of the invention one or more sensing elements and electronics may be on the same side of the substrate 16. The vias 18 may be arranged accordingly to effect electrical contact between one or more sensing elements and electronics, irrespective of the position of a sensing element and electronics on the substrate 16.

Figure 3:
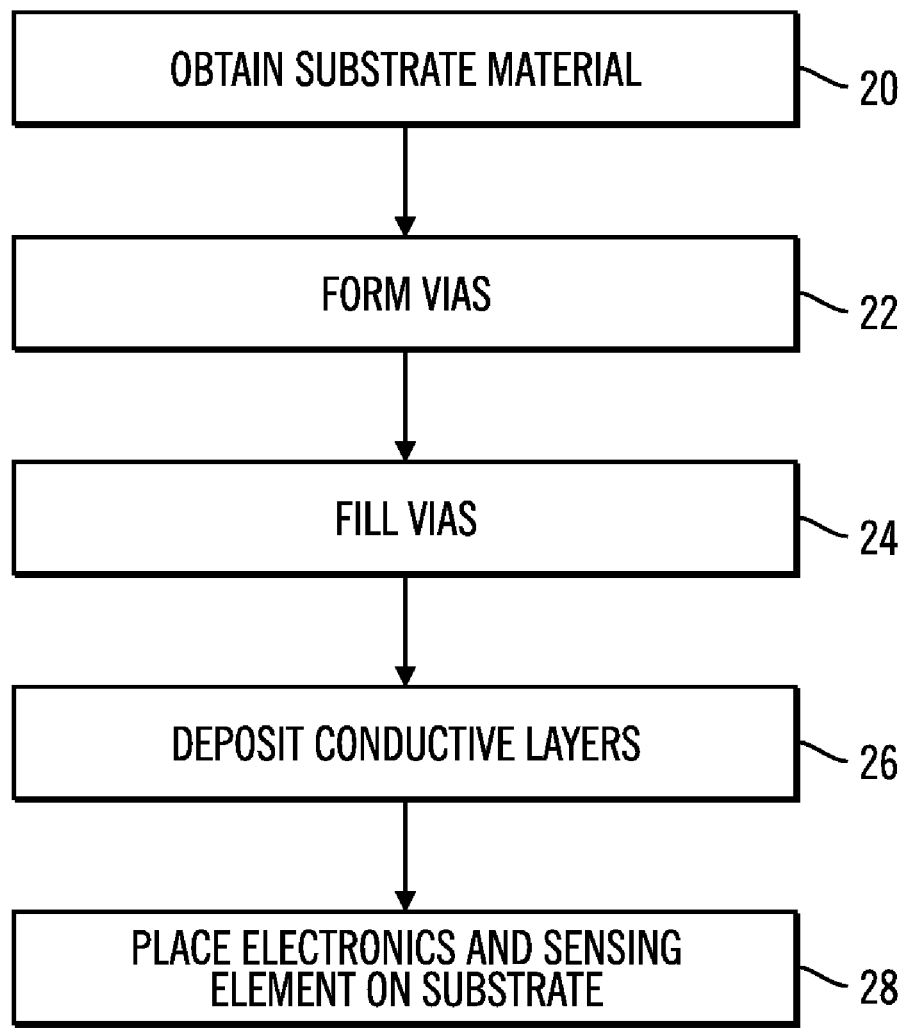
FIG. 3 is a flow diagram of a generalized process for fabricating a sensor substrate according to an embodiment of the present invention.

FIG. 3 shows a generalized process for fabricating a sensor substrate according to an embodiment of the present invention. Substrate material is obtained at step 20. At step 22, vias are formed in the substrate such that a hollow path is created from one side of the substrate to another. At step 24, the vias are filled with a material that is electrically conductive such that electrical continuity exists between one side of the substrate and another. In addition, the vias are filled such that a hermetic seal exists between one side of the substrate and another. At step 26, conductive layers are deposited onto each side of the substrate that make electrical contact with the vias. At step 28, electronics are placed on one side of the substrate and a sensing element is placed on another side of the substrate, both being placed in such a manner that they make the desired contact with the conductive layers.

Figure 4:
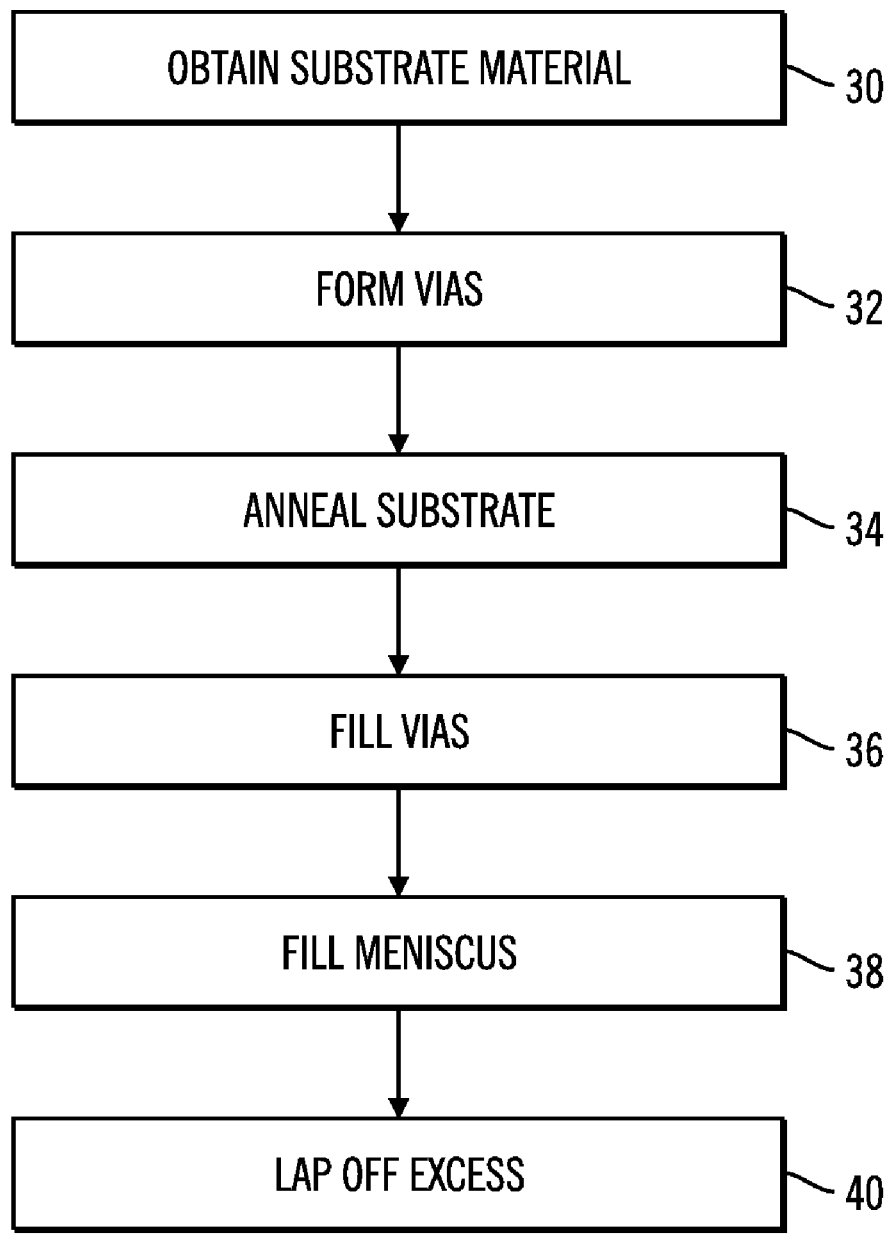
FIG. 4 is a flow diagram of a more detailed process for fabricating a sensor substrate according to an embodiment of the present invention.

FIG. 4 shows a more detailed process for fabricating a sensor substrate according to an embodiment of the present invention. Although the process detailed in FIG. 4 refers to a substrate, it is to be understood that the process may be applied to a plurality of substrates formed from a single board of substrate material.

A variety of fabrication techniques may be used during the fabrication of the sensor substrate. For example, either thin film or thick film fabrication technologies may be used. The generalized process shown in FIG. 4 is for purposes of illustration only, and should not limit embodiments of the invention in any way.

Substrate material is obtained at step 30. As stated previously, according to a typical embodiment of the present invention, a 92%-96% alumina substrate ($Al_2O_3$) may be used. Alumina is widely used in the microelectronics industry and is available from many resources. For example, a 96% alumina substrate may be purchased from COORS, INC.

Although 99.6% alumina is typical in electrode based sensor applications because of its purity, which typically results in enhanced device resistance, 92%-96% alumina may be used for embodiments of the present invention for enhanced performance during annealing and testing processes of embodiments of the present invention. On a substrate of greater than 96% alumina cracks resulting from laser drilling of the vias will not anneal as well as 92%-96% alumina.

A substrate of less than 92% alumina typically has a surface with increased roughness and granularity, making it difficult to print on and seal. In addition, testing of a substrate of less than 92% alumina may be difficult because the substrate surface may absorb helium used during leak detection and may be more susceptible to corrosion. Moreover, a substrate of less than 92% alumina is typically darker than 92%-96% alumina and may affect photolithography processes used in embodiments of the present invention.

At step 32, vias are formed in the surface of the substrate such that a hollow path is created from one side of the substrate to another. The vias may be laser drilled, punched or formed in other manners that are common in the industry.

At step 34, the substrate may be annealed. If the process used for forming vias results in cracks on the surface of or within the body of the substrate, annealing of the substrate may be required to mend such cracks. According to one embodiment of the present invention, the substrate is annealed at approximately 1200 C for approximately 16 hours. If the process used for forming vias does not result in cracks on the surface of or within the body of the substrate and hermeticity from one side of the substrate to another is possible without annealing, the annealing step may be avoided.

The vias are filled at step 36. The vias may be filled with any electrically conductive material that can be packed densely enough to provide hermeticity from one side of the substrate to another. The filler should be electrically conductive so that an electrically conductive path is formed from one side of the substrate to another, allowing electrical contact between components on each side of the substrate, such as, for example, sensor electrodes on one side of the substrate and electronic circuitry on another side.

According to one embodiment of the present invention, the vias may be filled with an electrically conductive filler. For example, the vias may be filled with a fritted or fritless ink, such as a gold or a platinum paste. Fritless ink is generally more desirable than fritted ink in this application because fritted ink typically comprises too many fillers and particulates to facilitate the formation of a densely packed via. In order to provide the hermeticity required from one side of the substrate to another, the filling of the via must be such that voids or gaps that would support the development of moisture do not exist within the material used to fill the via.

According to one embodiment of the present invention, a 96% alumina substrate, which may be purchased off the shelf from a variety of manufacturers, such as COORS, INC., may be filled with a gold paste. If another type of substrate is used, such as, for example, a 92% alumina substrate which may be custom made, the substrate may be purchased with the vias already filled with a filler, such as for example, platinum paste.

Figure 5:
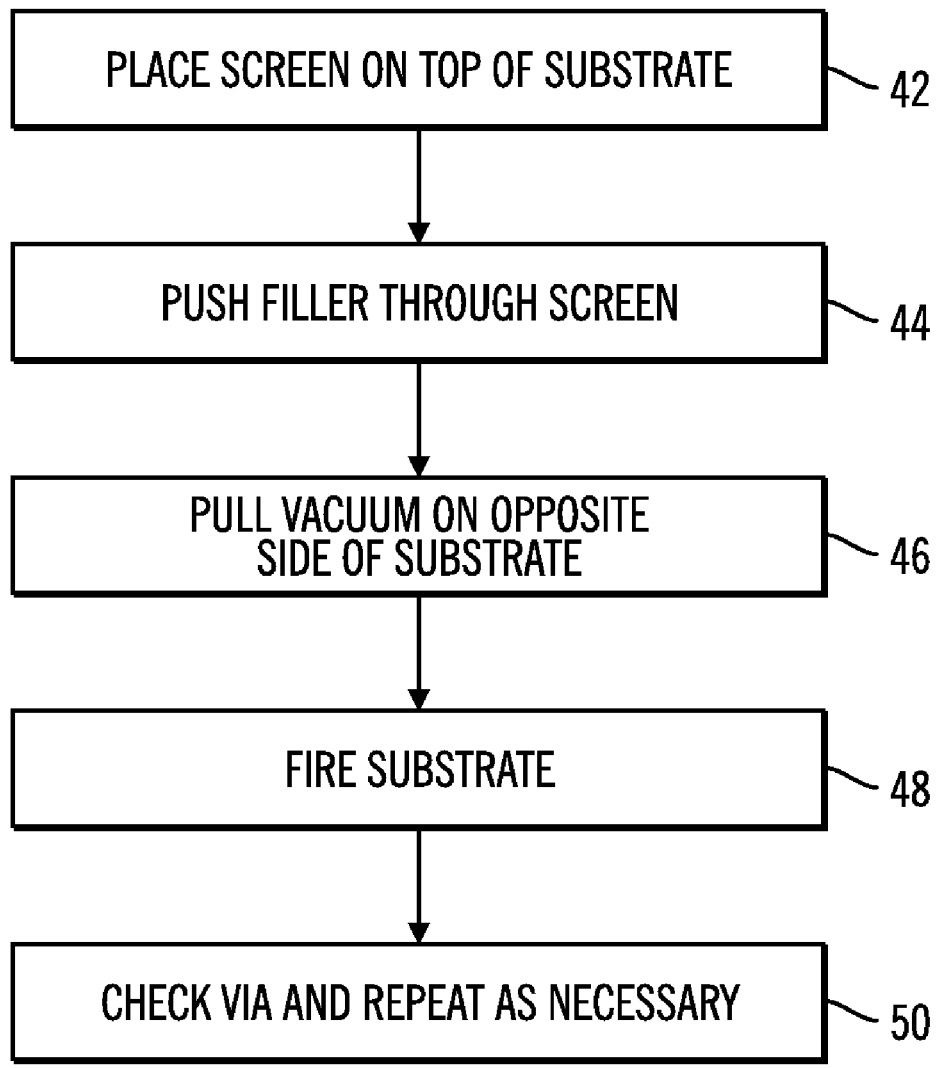
FIG. 5 is a flow diagram of a process for filling vias with a filler according to an embodiment of the present invention.

A process of filling vias with a filler according to an embodiment of the present invention is shown in FIG. 5. At step 42, a screen with a via pattern may be placed on top of the surface of the substrate. A stencil may also be used. At step 44, a filler, such as fritless ink, may be pushed through the screen into the via in a "squeegee" fashion. At step 46, a vacuum is pulled on a side of the substrate opposite the side on which the filler has been pushed into the via such that the filler coats the walls of the via. Filling vias in a vacuum facilitates intimate contact with surfaces and dense packing.

After the filler has coated the walls of the via in step 46, the substrate is fired in step 48 so that the filler is hardened, i.e., it becomes solid. At step 50, the via is checked to see if it is completely plugged. If the via is completely plugged, the process of filling the via according to an embodiment of the present invention is complete. If the via is not completely plugged, steps 42-48 may be repeated as many times as is necessary until the via is completely plugged with the filler.

Figure 6A:
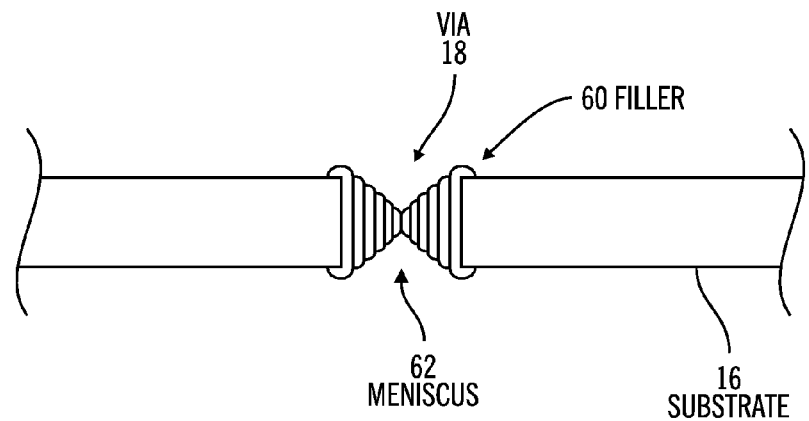
FIG. 6A is a cut-away view of a filled via according to an embodiment of the present invention.

A via 18 filled according to the process of FIG. 5 may be seen in FIG. 6A. A substrate 16 containing a via 18 has been filled with a filler 60. Successive applications of the filler 60 results in layers of the filler 60 extending throughout the hollow area of the via 18 until the filler 60 plugs the via 18 and eliminates any pathway from one side of the substrate 16 to another. A meniscus 62 typically forms on either side of the via 18 after the via 18 has been filled with the filler 60.

Returning to FIG. 4, the meniscus 62 that typically forms during the filling of the vias 18 may be filled at step 38. The meniscus 62 may be filled with the same filler 60 that was used to plug the vias 18.

Figure 7:
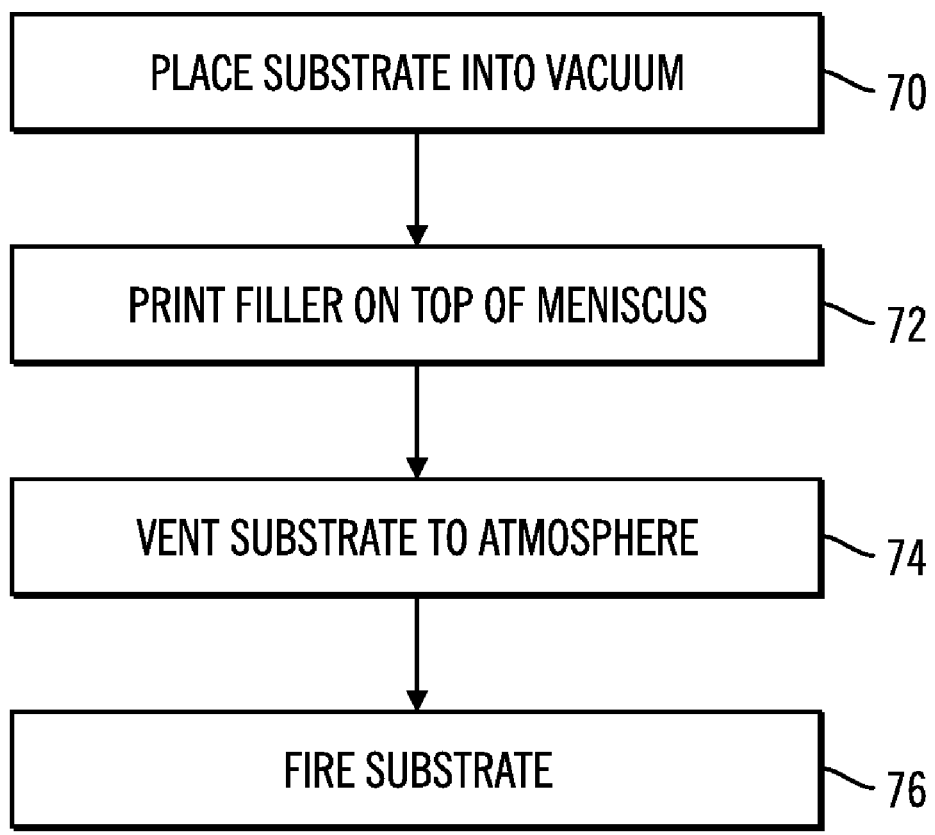
FIG. 7 is a flow diagram for filling a meniscus according to an embodiment of the present invention.

FIG. 7 shows a process for filling the meniscus 62 according to an embodiment of the invention. At step 70, the substrate 16 is put into a vacuum. At step 72, a filler 60 is printed onto the top of the meniscus 62. The printing process used may be the same process detailed in FIG. 5 for filling the vias 18 or may be another suitable process. At step 74, the substrate 16 is then vented to atmosphere. Venting the substrate 16 to the atmosphere introduces an atmospheric pressure on the filler 60, which pushes down on the filler 60 in the meniscus 62 and displaces any gap that might be in the meniscus 62 or via 18.

Figure 6B:
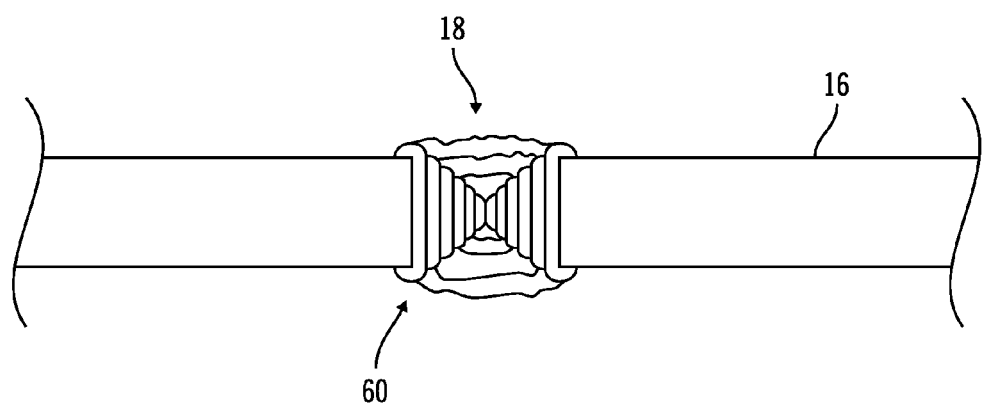
FIG. 6B is a cut-away view of a filled via and a filled meniscus according to an embodiment of the present invention.

At step 76, the substrate 16 is then fired such that the filler 60 in the meniscus 62 is hardened. Firing of the substrate also burns off any organics, solvents or other impurities. According to one embodiment of the present invention, if the filler 60 used is a fritless ink such as, for example, gold or platinum paste, the substrate 16 may be first fired at 300-400° C. to burn off organics, solvents or other impurities. The substrate 16 may then subsequently be fired at 900-1000° C. At 900-1000° C., the filler 60 may sinter. The firing time may typically be a few hours for every firing cycle. After firing the filler 60 such that it sinters, the substrate 16 may be cooled such that the filler 60 hardens. Cooling must be done at a rate slow enough such that the substrate 16 does not crack, which would compromise the hermeticity of the device. Steps 70-76 may be repeated as often as necessary to fill the meniscus 62 and the layers of filler 60 that extend above the substrate. A substrate 16 with a filled via 18 and a filled meniscus 62 may be seen in FIG. 6B.

Figure 8:
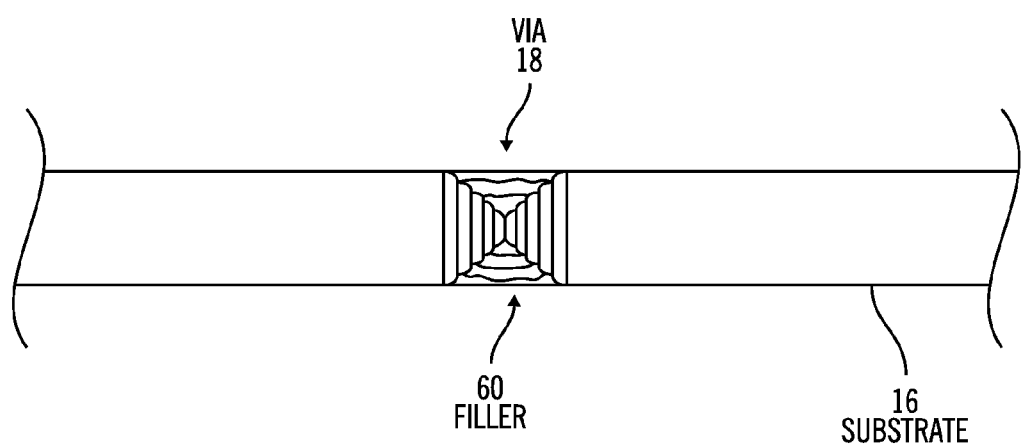
FIG. 8 is a cut-away view of a hermetically filled via with excess filler from a via and a meniscus lapped off according to an embodiment of the present invention.

Returning again to FIG. 4, at step 40 the excess filler 60 that extends above the surface of the substrate 16 resulting from the filling of the vias 18 and the meniscus 62 is lapped off so that the filler 60 is even with the surface of the substrate. The filler 60 may be lapped off using tools and techniques that are common in the industry so long as the hermetic integrity of the substrate 16 is not compromised. A substrate 16 with excess filler 60 lapped off and hermetically sealed vias 18 is shown in FIG. 8.

Thus, subsequent to step 40 in FIG. 4, a process according to embodiments of the present invention has generated a substrate 16 that is hermetically sealed from one side to another. It should be understood at this point that the fabrication of the substrate 16 for hermeticity is not limited to the process described in FIG. 4. Other steps or processes may be introduced, or steps may be eliminated, without departing from the spirit and scope of embodiments of the present invention. For example, depending on the type of filler 60 used to fill the vias 18 and the meniscus 62, it may be possible to carry out the annealing steps and the firing steps at the same time. Other variations in the process are also possible while still maintaining the essence of embodiments of the present invention.

The substrate 16, with hermetically sealed vias 18, may be used for a variety of applications. According to embodiments of the present invention, the substrate 16 may now be prepared to accept a sensing element on one side of the substrate and electronics on another side of the substrate 16. As before, the substrate 16 may be prepared using a variety of techniques, including, for example, thin film or thick film deposition processes. For purposes of illustration, and not by way of limitation, processes according to embodiments of the present invention will be described below using thin film deposition techniques.

Electronics may be affixed to one side of the substrate 16 and may take a variety of forms. For example, the electronics may take the form of an integrated circuit (IC), such as, for example, an ASIC, a microcontroller, or a microprocessor. Alternatively, the electronics may take the form of discrete components.

Figure 9:
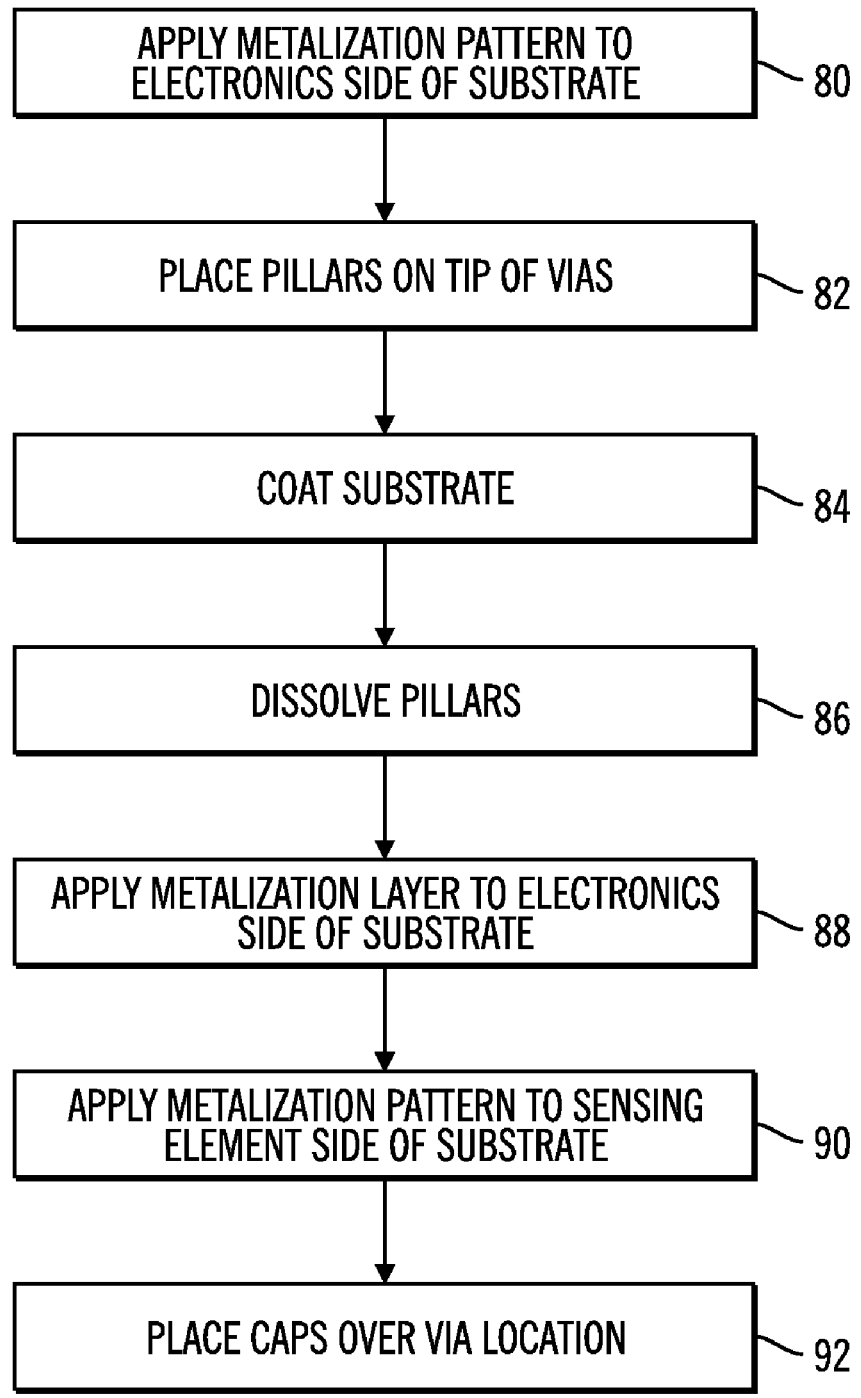
FIG. 9 is a flow diagram of a process for preparing one side of a substrate to accept an IC and another side to accept a sensing element according an embodiment of the present invention.

In addition, a sensing element may be affixed to another side of the substrate 16. FIG. 9 shows a process according to embodiments of the present invention for preparing one side of the substrate 16 to accept an IC and another side to accept a sensing element.

At step 80, a side of the substrate 16 being prepared for an IC may have a metalization pattern applied to it using standard resist photolithography or other techniques common in the industry. This layer of metalization is the conductor that provides continuity from the portion of a via 18 on the sensing element side of the substrate 16 to a bonding pad on an IC side of the substrate 16. In practice, this layer may actually be two, three, or more layers. For example, the metalization layer may be a titanium-platinum layer. Alternatively, the metalization layer may be a titanium-platinum-titanium layer. The pattern may correspond to the pins of the IC or may be some other pattern depending on the desired application.

At step 82, aluminum pillars may be placed on top of the vias. A ceramic or other material mask may be laser drilled, punched or otherwise worked to form openings corresponding to the via pattern on the substrate. According to one embodiment of the present invention, the openings may be 20-25 microns deep. The mask may then affixed to the substrate on top of the metalization pattern applied during step 80. Aluminum is then deposited through the openings to form pillars 20-25 microns high. Once the pillars have been formed, the mask is removed, leaving the 20-25 micron aluminum pillars on top of the vias. A substrate 16 with aluminum pillars 100 formed on top of the vias 18 according to an embodiment of the present invention may be seen in FIG. 10A.

After step 82, the entire substrate may be coated with an alumina coating at step 84. According to one embodiment of the present invention, the entire substrate may be put into a vacuum chamber and blanket coated with an alumina coating. A variety of processes may be used to blanket coat the substrate with alumina. For example, chemical vapor deposition (CVD), epitaxial deposition, sputtering or evaporation may be used to blanket coat the substrate with the alumina coating. Alternatively, ion beam assist deposition (IBAD) may be used. IBAD is a combination of two distinct operations: physical vapor deposition combined with bombarding the substrate surface with low energy ions. Bombarding the substrate surface with low energy ions allows for better adhesion and higher density of the alumina coating.

Using an IBAD process to coat the substrate with alumina gives pin-hole free layers of alumina, which enhances the overall hermeticity of the device. In other words, coating the substrate with alumina using the IBAD process prevents the transmission of vapor, moisture, fluids or other elements that would compromise the hermetic integrity of the device.

According to one embodiment of the invention, the alumina coating may be 12 microns deep. Consequently, at the end of step 84, the substrate will have aluminum pillars rising 8-13 microns above a 12 micron alumina sheet. A configuration according to this embodiment of the present invention may be seen in FIG. 10B.

At step 86, the entire substrate, including the alumina coating and the aluminum pillars, is put into a dissolving solution such as, for example, ferric chloride (FeCl$_3$) or other solution that is strong enough to dissolve the aluminum pillars but mild enough not to attack the alumina coating. Thus, after the aluminum pillars dissolve, the substrate will be covered with an alumina coating 12 microns high with recesses permitting access to the vias. This configuration may be seen in FIG. 10C.

At step 88, the metalization layer supporting the IC and any other components being affixed to the electronics side of the substrate may be applied. Any suitable metal may be applied using any suitable process. For example, a metalization using gold may be applied with a thin film process. The pattern may take a variety of shapes. For example, according to one embodiment of the invention, the pattern may resemble a "ring" or a "racetrack." In addition, the gold may fill the recesses created by the aluminum pillars that were previously dissolved. Hermeticity will generally not be required at this layer since the substrate has already, up to this point in the process according to embodiments of the present invention, been hermetically sealed. Accordingly, the metalization layer may be 6000 to 10000 angstroms. Once this layer of metalization has been applied, the IC, and any other components, such as, for example, capacitors, may be wired bonded or otherwise connected to the pads. Additionally, any other component, such as a lid for the electronics, for example, may be affixed to the electronics side of the substrate subsequent to step 88.

At step 90, a side of the substrate 16 being prepared for a sensing element may have a metalization pattern applied to it. A variety of techniques may be used to apply the metalization pattern. For example, a metalization pattern may be applied to the substrate 16 by etching it onto the substrate 16. Alternatively, a metalization pattern may be applied to the substrate 16 using common photoresist techniques.

Figure 11:
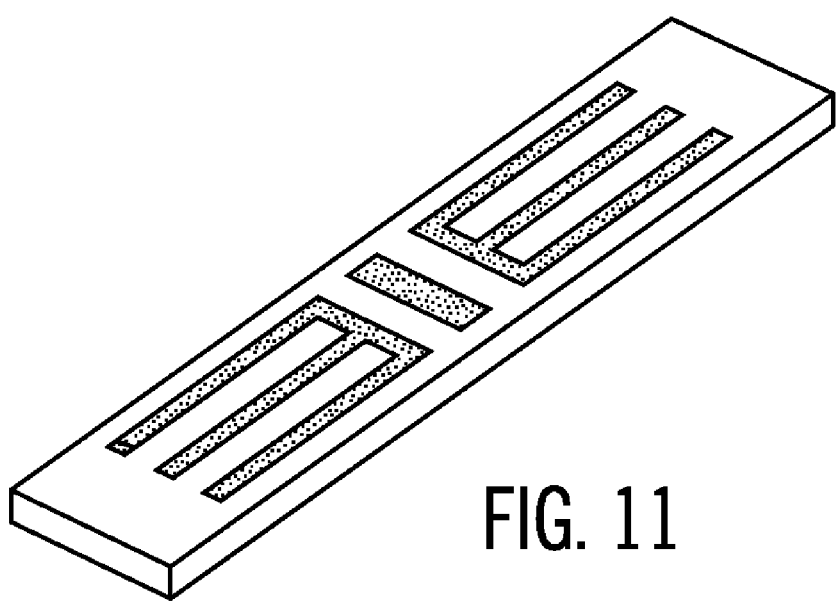
FIG. 11 is a perspective view of a photoresist corresponding to an electrode pattern according to an embodiment of the invention.

According to one embodiment of the invention, if common photoresist techniques are used, a photoresist may first be applied to the substrate. The photoresist may be a positive resist, which becomes soluble when light it interacts with light, or a negative resist, which becomes insoluble when it interacts with light. If a positive resist is used, a mask may be put over the photoresist and the mask and the photoresist may then be exposed to light. Thus, light going through openings on the mask solublizes the unmasked portions of the photoresist. The mask may then be washed off, and, consequently, the substrate will have a cured coating of photoresist where the unmasked photoresist was exposed to light. A photoresist corresponding to an electrode pattern according to one embodiment of the invention may be seen in FIG. 11. The electrodes have tie bars to provide a conductive path for electroplating. The working and counter electrodes are metalized.

The cured photoresist may then be metalized using a variety of techniques. Any thin film deposition technique may be used, such as, for example, sputtering. Thus, according to one embodiment of the invention, the substrate may be put into a vacuum, then, first sputtered with a first metal, such as, for example, titanium, then sputtered with a second metal, such as, for example, platinum. Accordingly, a conductive layer may be placed between the vias and alumina caps in order to maintain electrical conductivity.

The photoresist may then be washed away. For example, the photoresist may be put into an acetone ultrasonic bath. Thus, the phototresist that wasn't cured during exposure to light due to the mask will dissolve and the metal that was deposited on the uncured photoresist will be washed away.

At step 92, caps may be placed over the via locations. Oxygen reduction occurs at the working electrodes and creates hydroxyl ions, thus creating an alkaline local environment. As the device operates, the hydroxyl ions attack the electrode/via interface, which is initially hermetic but which can be broken down if the hydroxyl ions interact with the via for an extended period. Thus, to extend via life a cap is placed over the via to keep current from the electrochemical process of the hydroxyl ions from entering the via, thus extending via life and improving via reliability. In other words, caps may be used to prevent byproducts of detection electrochemistry from compromising via hermeticity by preventing corrosive attack of both the via and the annealed surfaces of a laser drilled opening.

A variety of techniques may be used to place a cap over the vias. For example, alumina caps may be deposited over the via using an IBAD process. A shadow mask may be used during the process similar to the technique used to apply the aluminum pillars. Caps may be formed with a positive shadow mask, which may be used where alumina deposited through an aperture remains in place on a finished substrate. The cap position may be adjusted, i.e., it's length may be adjusted along the electrode, changing the configuration of the active electrodes to the windows. The sensitivity of the sensor can depend on the cap position, or the resulting position of the active electrode to the window.

As an alternative to placing caps over vias, caps may be placed over electrodes to inhibit oxygen reduction at the electrodes. According to embodiments of the invention, caps placed over the vias or the electrodes may be about 18 microns in thickness.

Figure 12:
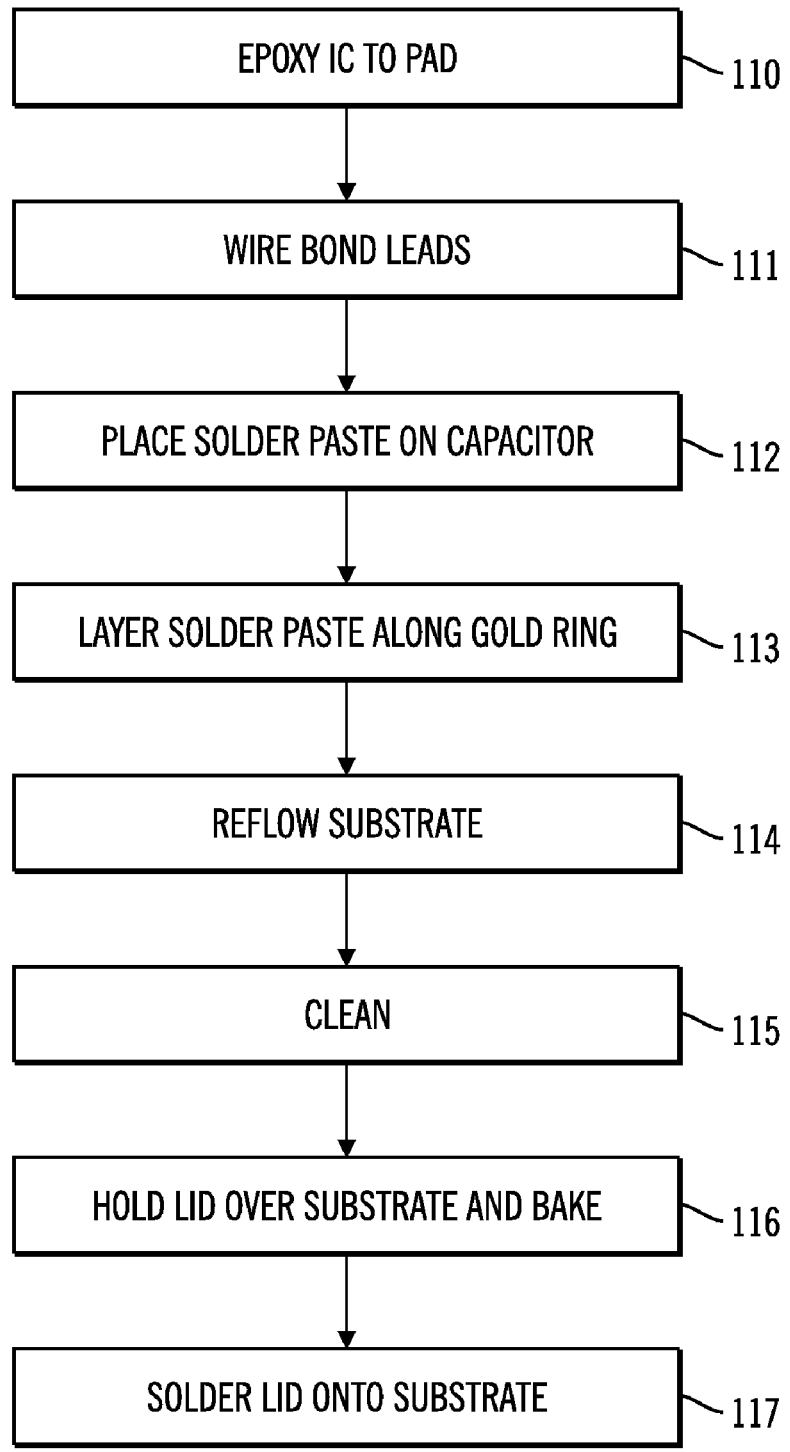
FIG. 12 is a flow diagram of a process for affixing an IC to an electronics side of a substrate according to an embodiment of the present invention.

Once an electronics side of the substrate 16 and a sensing element side of the substrate 16 has been prepared to accept electronics and a sensing element, respectively, electronics and a sensing element may be affixed to the substrate. A process for affixing an IC to the electronics side of the substrate 16 is shown in FIG. 12.

At step 110, an IC may be epoxied to a rectangular pad in the center of the substrate. At step 111, the leads of the IC may be wired bonded to the gold pads earlier formed on the electronics side of the substrate.

According to some embodiments of the invention, a capacitor may be used in connection with the IC. The capacitor may serve as a power supply instead of a battery and may be large enough to maintain a DC voltage in between pulses. If a capacitor is used, at step 112 a solder paste may be placed on the capacitor and the capacitor may be put into position on the substrate.

At step 113, a layer of solder paste may be placed along the entire gold ring previously deposited on the electronics side of the substrate. At step 114, the entire substrate may be reflowed at temperature, including the solder paste deposited on the gold ring. The entire substrate may then be put through cleaning cycles at step 115 to remove residual material, such as flux residue from solder paste.

According to one embodiment of the invention, a lid may be placed over the electronics. At step 116, the lid may be held by a fixture over the substrate and the substrate may be baked to remove moisture. For example, the substrate may be baked at 150° C. for 12 hours at less than 1 torr to reduce moisture to 5000 ppm or less.

At step 117, the lid may be soldered onto the substrate. The lid may be formed from a solid gold sheet, typically about 3 mils thick. It may also include a bathtub shaped lip. After the baking process of step 116, the lid and substrate may be put into a helium atmosphere (some helium, such as, for example, 1 atmosphere, may be left in the lid for reasons to be discussed below in connection with leak testing) with very low oxygen and very low moisture. Thus, because of the solderability of gold and the absence of any oxidation due to the low oxygen atmosphere, the lid may be soldered onto the electronics side of the substrate without using solder without flux. Consequently, no flux residue will exist on the substrate subsequent to soldering the lid to the substrate. The absence of any residue on the substrate is desirable because any residue may promote condensation or water vapor between IC pads, thus providing a leakage path. On an IC, there is typically only a 0.002-0.003 space between IC pads. Also, leakage currents should be kept less than 50 pico amps in order to be distinguishable from the currents generate by an electrochemical cell used as a sensing element.

Figure 13:
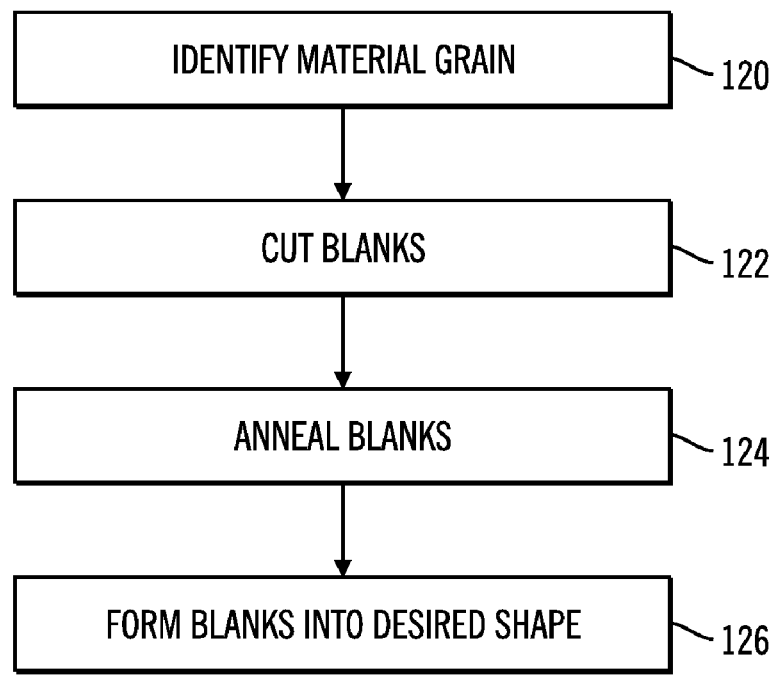
FIG. 13 is a flow diagram of a process for forming a lid according to an embodiment of the present invention.

A process for forming a lid is shown in FIG. 13. In order to prevent the lid from tearing and developing holes, the grain of the material may be identified such that a blank may be properly cut and annealed. Thus, the proper malleability of the material may be achieved. The grain may be due to mechanical stress from a rolling process. Accordingly, at step 120, a grain of a material is identified. According to one embodiment of the invention, the longer dimension of the material is identified. At step 122, blanks squares or rectangles are cut from the material. The blanks may be annealed at step 124. At step 126, the blanks may be formed into the desired shape.

If gold is the material used, step 126 is speed controlled because gold hardens very quickly. Also, if the form of the lid is to be a bathtub shape as described above, the lid may have a small flange to provide a good seal. The flange may be 4-5 mils thick, or a wider dimension than the thickness of the area of the electronics on the electronics side of the substrate (for example, the gold track on the substrate may be 4 mils wide). Thick, wide lid walls may be used as an alternative to the flange. Also, the lid may have a small draft to allow a capacitor to be near its end.

Figure 14:
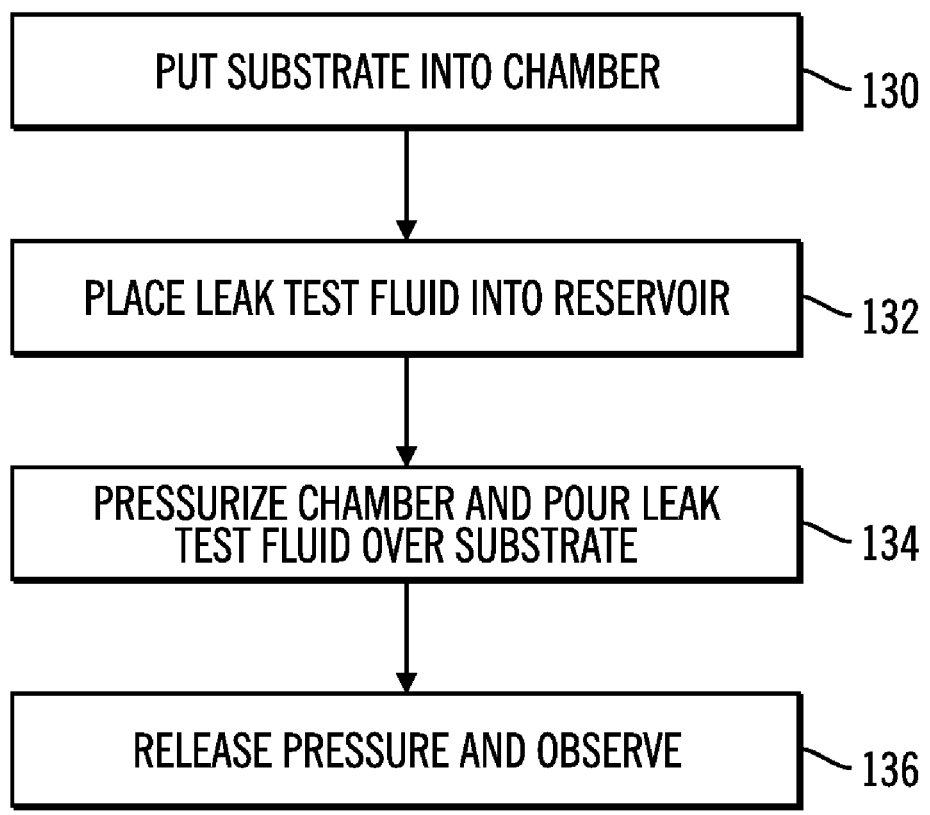
FIG. 14 is a flow diagram of a process for performing a gross leak test according to an embodiment of the present invention.

The substrate may be subjected to leak testing. Gross leak testing and fine leak testing may be performed. Leak testing may be performed in a variety of ways. For example, a process for performing a gross leak test according to an embodiment of the present invention is shown in FIG. 14. At step 130, the substrate may be put into a chamber. According to one embodiment of the invention, the chamber may have a recess for the substrate and a reservoir for a leak test fluid, such as, for example, freon. At step 132, the leak test fluid is placed in the reservoir. At step 134, the chamber is pressurized with helium and the leak test fluid is poured into the recess. For example, the chamber may be pressurized at 150 psi (10 atmospheres) and kept at this level for 12 hours. At step 136, the pressure is released and the fluid is observed for bubbles. An absence of bubbles indicates that there are no gross leaks in the substrate.

After the gross leak test has been successfully performed, a fine leak test may be performed. For example, a process for performing a fine leak test according to an embodiment of the present invention may include putting the substrate into a vacuum chamber and observing helium leaks with a mass spectrometer. Helium exists in the lid previously attached to the electronics side of the substrate. Thus, any helium observed may indicate a fine leak in the substrate.

Figure 15:
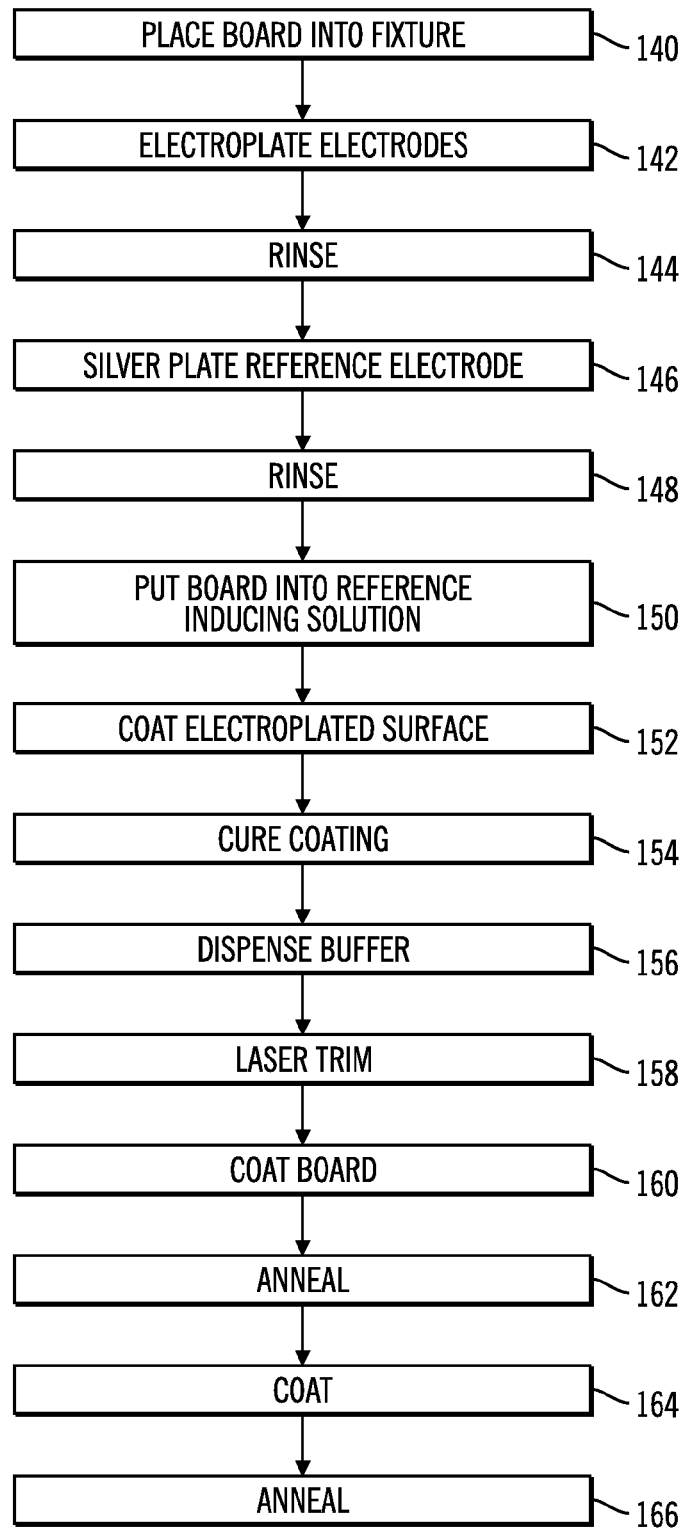
FIG. 15 is a flow diagram of a process for electroplating and coating the substrate according to an embodiment of the present invention.

Once a substrate has passed both a gross leak test and a fine leak test, the substrate may be put through a final electroplating and coating process. A process for electroplating and coating the substrate according to an embodiment of the present invention is shown in FIG. 15. To describe the process according to the embodiment of the present invention shown in FIG. 15, the description will refer to a board of substrate material from which a plurality of substrates may be formed.

At step 140, the board may be placed into a fixture for electroplating. At step 142, the electrodes may be electroplated with a metal. For example, a noble metal probe may be used to deposit a first solution of chloroplatinic acid onto the electrodes, i.e., platinum may be deposited onto the electrodes. This is typically called platinum blackening. According to one embodiment of the invention, four out of the five electrodes, i.e., the first and second working electrodes and the first and second counter electrodes may be blackened with platinum. After the electrodes have been blackened with platinum, the board may be rinsed at step 144. A variety of fluids may be used to rinse the board.

At step 146, according to an embodiment of the present invention, the reference electrode may be silver plated using a silver plating solution. At step 148, the board may be rinsed again.

At step 150, the board may be put into a solution, such as, for example, a dilute hydrochloric acid solution, to make an electrochemical reference. According to one embodiment of the present invention, the hydrochloric acid will react with the reference electrode and the counter electrodes, generating a potential difference between the reference electrode and the counter electrodes that may be used as a reference voltage.

At step 152, the surface of the board that has been electroplated may be coated. A variety of techniques may be used to coat the surface of the board. For example, the surface of the board may be spin coated using a polymer such as hydroxyethel methacholate (HEMA) or polyhydroxyethel methacholate (PHEMA). This coating may form the basis of an electrolyte layer that defines how much oxygen may flow to an electrode. It may act like a valve and may be flow insensitive such that the amount of oxygen flowing to the electrode remains substantially constant.

At step 154, the coating may be cured using a photomask, such as a negative photoresist, and exposure to ultraviolet light. At step 156, a sterile bicarbonate buffer may be dispensed onto the polymer. The buffer may be isotonic such that it inhibits communication with water and provides for an osmotic exchange. The buffer may also have sodium chloride in it such that it provides electrolytic properties to the polymer. According to an embodiment of the present invention, small drops may be placed onto the polymer such that the drops do not flow over the side of the board. The spaces between the drops may be filled in with more drops and the drops may soak into the polymer.

At step 158, the board may be laser trimmed to remove all traces connecting the electrodes. Thus, subsequent to step 158, the electrodes will be separated. At step 160, the board may be coated again using any of a variety of techniques, such as spin coating, with an adhesion promoter, such as silane.

At step 162, the coating applied at step 160 may be annealed so that the coating cures. At step 164, the board may be yet again coated using any of a variety of techniques, such as spin coating, with an insulating material, such as silicon rubber, and annealed again at step 166. Steps 164 and 166 prevent fluid components, such as those that may be found in blood, from penetrating any circuitry on the substrate. In addition, using steps 164 and 166, electric currents remain within the boundaries of the substrate.

Figure 16:
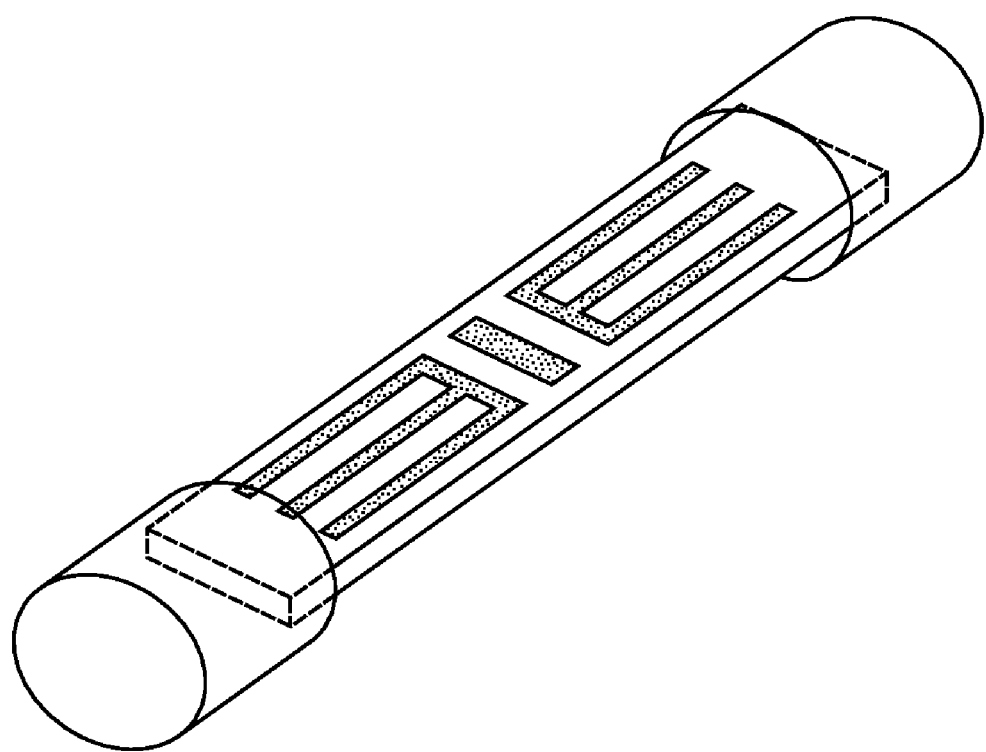
FIG. 16 is a perspective view of a finally assembled sensor substrate according to an embodiment of the invention.

Subsequent to step 166, the board is complete. The completed board may be separated into individual modules. For example, the completed board may be put onto a waxed glass plate and diced with a dicing saw to cut the individual modules. At step 166, leads that may extend to another device such as a pump or other electronics may be welded onto each module. Additionally, end caps or beads, which may be formed from molded silicon, may be placed at the end of each module. A finally assembled sensor substrate may be seen in FIG. 16. According to one embodiment of the invention, ninety-four modules may be made from a board with dimensions two inches by two inches.

Figure 17:
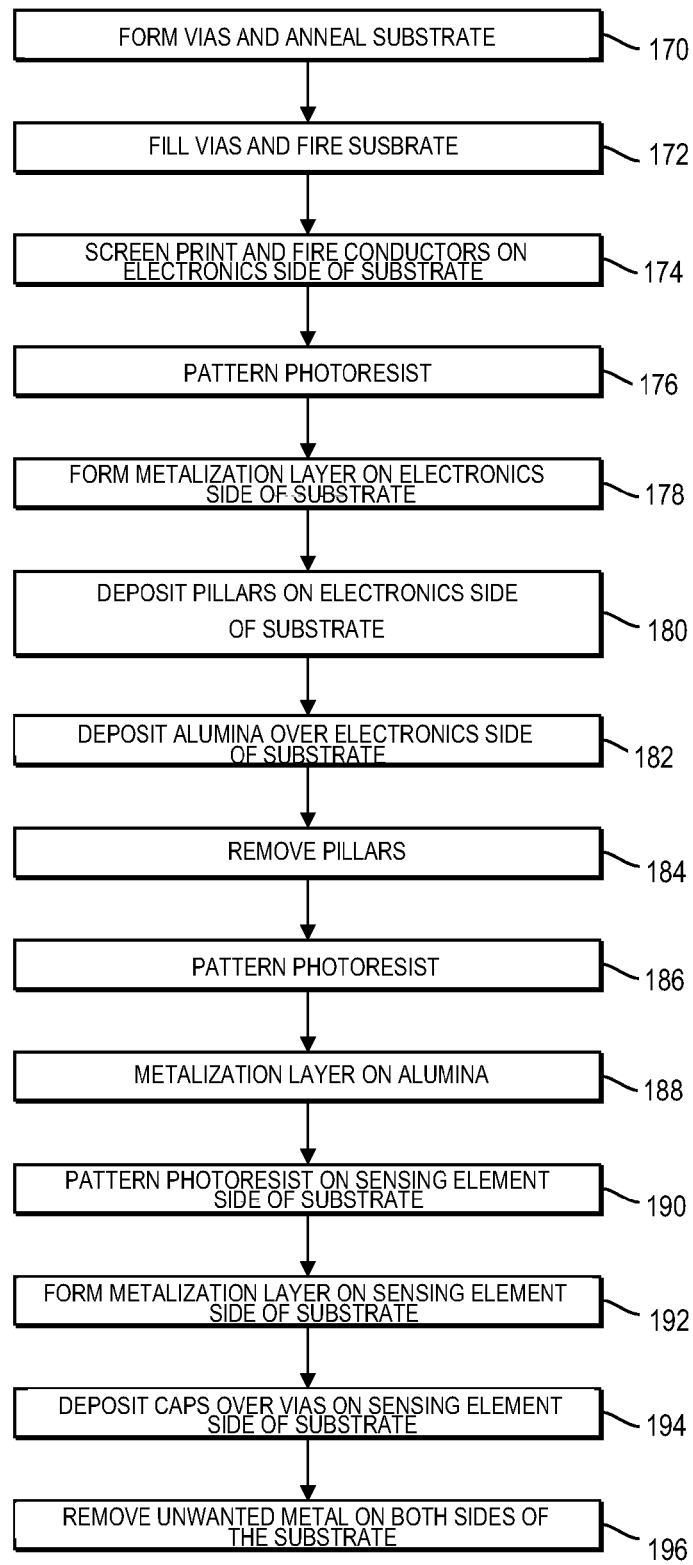
FIG. 17 is a flow diagram of a generalized process for fabricating a sensor substrate according to an embodiment of the present invention.

A generalized process for fabricating a substrate according to another embodiment of the invention may be seen in FIG. 17. At step 170, vias may be formed on a substrate and the substrate may be annealed. The vias may be formed using laser drilling. The substrate may be a 92%-96% alumina substrate.

At step 172 the vias may be filled and the substrate fired. The vias may be filled with a variety of conductive materials such as, for example, gold or platinum. In addition, the vias may be filled using a vacuum screen printing process. Step 172 may be repeated until the vias are filled. Once the vias are filled, they may be checked for hermeticity.

At step 174, an electronics side of the substrate may be screen printed and conductors may be fired upon it. According to one embodiment of the invention, the conductors may be fired using platinum and a thick film process.

At step 176, a photoresist may be patterned on the electronics side of the substrate. Next, at step 178, a metalization layer may be formed on the electronics side of the substrate. For example, titanium and platinum may be deposited on the electronics side of the substrate using a DC sputtering process. The photoresist may then be lifted from the substrate.

At step 180, aluminum pillars may be deposited on the electronics side of the substrate. According to an embodiment of the invention, the aluminum pillars may be 30-micron pillars and may be deposited using a shadow mask and a vacuum evaporation technique.

At step 182, alumina may be deposited over the electronics side of the substrate. The alumina deposited may be an 18 micron layer over the entire side of the substrate and may be deposited using an ion beam assisted vacuum evaporation process.

At step 184, the pillars deposited at step 180 may be removed using ferric chloride. At step 186, a photoresist may be patterned on top of the 18-micron layer of alumina.

At step 188, another metalization layer may be placed on top of the alumina surface. According to an embodiment of the invention, titanium, platinum and gold may be deposited on top of the alumina surface using a DC sputtering process. The photoresist may then be lifted from the substrate.

At step 190, a photoresist may be patterned on a sensing element side of the substrate. The sensing element side of the substrate may or may not be the same side as the electronics side of the substrate. At step 192, a metalization layer may be formed on the sensing element side of the substrate. According to one embodiment of the invention, titanium and platinum may be deposited on the sensing element side of the substrate using a DC sputtering process. The photoresist may then be lifted from the substrate.

At step 194, caps may be deposited over the vias. According to one embodiment of the invention, a shadow mask may be used to deposit 18-micron alumina caps over vias projected on the sensing element side of the substrate using an ion beam assisted vacuum evaporation technique.

At step 196, unwanted metal existing on either the electronics side of the substrate or the sensing element side of the substrate may be removed. According to one embodiment of the invention, unwanted metal may be removed using a shadow mask and an ion mill etching process.

As stated previously, according to an embodiment of the present invention, forming IBAD caps on an electrode side of the substrate may be done with a positive shadow mask. A positive shadow mask may be used where alumna deposited through an aperture remains in place on a finished substrate. A negative shadow mask may be used for applications where apertures or openings define regions which remain free of IBAD aluminum coatings. According to an embodiment of the invention, the use of positive and negative imaging of IBAD alumina along with screen-printing via filling and conductor application, and photo resist based thin film metalization creates a substrate possessing conductor and insulator geometries along with materials properties which support chronic, continuous sensing applications and microelectronics packaging in harsh environments such as, for example, the blood stream.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method of forming an hermetically sealed substrate comprising:
    obtaining a substrate material;
    forming a via from a first side of the substrate to a second side of the substrate;
    filling the via with a conductive material such that an hermetic seal forms between the first side of the substrate and the second side of the substrate to form a filled via; and
    depositing a pillar on top of the filled via,
    wherein depositing a pillar on top of the filled via comprises:
        depositing a metal on at least one of the substrate and the filled via;
        coating the substrate with a ceramic; and
        removing the metal after the substrate has been coated with the ceramic.

2. The method according to claim 1, wherein forming a via comprises laser drilling the via.

3. The method according to claim 1, wherein forming a via further comprises annealing the substrate.

4. The method according to claim 1, wherein filling the via comprises
    placing a screen on a surface of the substrate;
    pushing the conductive material through the screen such that the conductive material proceeds into the via; and
    pulling a vacuum on a side of the substrate opposite the side on which the conductive material has been pushed into the via such that the conductive material coats a wall of the via.

5. The method according to claim 4, wherein filling the via further comprises filling a meniscus that forms within the via.

6. The method according to claim 5, wherein filling a meniscus comprises
    putting the substrate into a vacuum;
    printing a conductive material into the meniscus; and
    venting the substrate to atmosphere.

7. The method according to claim 6, wherein filling a meniscus further comprises firing the substrate.

8. The method according to claim 1, wherein removing the metal comprises dissolving the metal after the substrate has been coated with the ceramic.

9. The method according to claim 1, wherein the ceramic coating is shorter than the pillar.

10. The method according to claim 1, further comprising covering the filled via with a cap.

11. A method of forming an hermetically sealed substrate comprising:
    obtaining a substrate material;
    forming a via from a first side of the substrate to a second side of the substrate;
    filling the via with a conductive material such that an hermetic seal forms between the first side of the substrate and the second side of the substrate to form a filled via; and
    covering the filled via with a nonconductive cap,
    wherein covering the filled via is done using an ion beam assist deposition process.

12. The method according to claim 4, wherein a stencil is used in place of the screen.

13. The method according to claim 1, wherein depositing a metal comprises:
    affixing a mask to the substrate before depositing the metal; and
    removing the mask after depositing the metal.

14. The method according to claim 1, wherein depositing a pillar on top of the filled via comprises:
    applying a metalized pattern on the substrate.

15. The method according to claim 14, wherein the metal is deposited on the metalized pattern on the substrate.

* * * * *